(12) United States Patent
Marcoz et al.

(10) Patent No.: US 12,070,585 B2
(45) Date of Patent: Aug. 27, 2024

(54) DOSE CONTROL DEVICE FOR INJECTABLE-DRUG DELIVERY DEVICES

(71) Applicant: BIOCORP PRODUCTION S.A., Issoire (FR)

(72) Inventors: Alain Marcoz, Montmorin (FR); Alexandre Pereira, Perignat-les-Sarlieve (FR); Mathieu Pollard, Pont du Chateau (FR)

(73) Assignee: Biocorp Production S.A., Issoire (FR)

( * ) Notice: Subject to any disclaimer, the term of this patent is extended or adjusted under 35 U.S.C. 154(b) by 1018 days.

(21) Appl. No.: 16/979,636

(22) PCT Filed: Mar. 13, 2019

(86) PCT No.: PCT/IB2019/052028
§ 371 (c)(1),
(2) Date: Oct. 21, 2020

(87) PCT Pub. No.: WO2019/175790
PCT Pub. Date: Sep. 19, 2019

(65) Prior Publication Data
US 2021/0038825 A1 Feb. 11, 2021

(30) Foreign Application Priority Data
Mar. 14, 2018 (WO) ................. PCT/IB2018/000426

(51) Int. Cl.
*A61M 5/315* (2006.01)

(52) U.S. Cl.
CPC . *A61M 5/31551* (2013.01); *A61M 2205/3317* (2013.01); *A61M 2205/3561* (2013.01); *A61M 2205/50* (2013.01)

(58) Field of Classification Search
CPC ............ A61M 5/31551; A61M 5/3155; A61M 5/31548; A61M 5/31556; A61M 5/31566; A61M 2205/3317
See application file for complete search history.

(56) References Cited

U.S. PATENT DOCUMENTS

2020/0061299 A1* 2/2020 Toporek ............ A61M 5/31593
2020/0114087 A1* 4/2020 Bauer ............... A61M 5/31528

* cited by examiner

*Primary Examiner* — Laura A Bouchelle
*Assistant Examiner* — Sarah Dympna Grasmeder
(74) *Attorney, Agent, or Firm* — Verrill Dana, LLP

(57) ABSTRACT

Dose control device for a handheld pen-type injectable-drug delivery device, the handheld pen-type injectable-drug delivery device comprising an elongate body with a proximal and distal extremity, a longitudinal axis extending from the proximal extremity to the distal extremity, and a rotatable dose setting wheel located at the proximal extremity, wherein the dose control device comprises a magnetic field producing mechanism located at the proximal extremity of the elongate body; one or more magnetic field sensors in communication with a data processing unit located on an outer surface of, or inside, the elongate body; and a clutch assembly configured to selectively move the magnetic field producing mechanism from a first, engaged, position, to a second, disengaged, position.

19 Claims, 6 Drawing Sheets

DOSE CONTROL DEVICE FOR INJECTABLE-DRUG DELIVERY DEVICES

The present invention relates to the field of injectable-drug delivery devices, and in particular, to dose control systems provided for such injectable-drug delivery devices.

Delivery devices for injectable drugs have been known for many years. As demands have progressed and evolved for more patient responsibility in the management of their own individual treatments and medication plans, various drug delivery devices have been developed that allowed a user to self-inject their drug. This is particularly the case, for example, with insulin, intended to treat the consequences of diabetes. However, other drugs also fall into this category, required for example, to address potentially life-threatening situations, and enabling immediate emergency injection of a required drug, such as anaphylactic shock treatments, anti-coagulants, opioid receptor agonists and antagonists, and the like, to the extent that it has become a common occurrence for patients suffering from, or susceptible to, such ailments to carry these devices around with them.

One of the known problems with the existing self-injector systems was that of accurate and precise dosage control. In previous generations of injectable-drug delivery devices, such devices were equipped with mechanical means in order to attempt to prevent or limit excessive dose injections, or over use of the device, and the potentially serious consequences of such abuse, misuse, or simply user error. Additionally, it was felt desirable to be able to inform the user how much of the drug they had self-injected, so that there might be at least some visible cue as the injected amounts, thereby facilitating management of the treatment regime.

The main problems associated with the mechanical solutions proposed was that they necessarily over-complexified the structure of the drug deliver devices, and quite often imposed a very strict or complicated modus operandi on the user, which often could be different to that to which the user was accustomed, thereby leading to yet further manipulation errors, lost drug doses, patient non-compliance, and numerous other difficulties.

To counter these difficulties, attempts were made to address the complex nature of purely mechanical solutions involving moving mechanical parts and mechanical interactions of small and fragile components, through the use of contactless sensors and an information processing system built into the device to indicate the frequency and dose amounts of injectable drug administered, wasted, purged or otherwise expelled from the drug delivery device. This led to multiple different technical solutions, however, each one was geared to the specifics of the particular manufacturer's corresponding range of injectable-drug delivery devices.

In other embodiments, the sensor circuitry can include position sensors adapted to monitor specific components of the drive mechanism which move during injection. The position sensors can be either linear sensors or rotary sensors, the particular choice of sensors being selected in accordance with the specific design of the dose setting and injection mechanism. For example, a linear position sensor can be provided that monitors the movements of the piston rod during injection. Alternatively, position sensors are provided which record the movements of a component which moves in synchronism with the piston rod during injection. For example, a component being rotatably mounted in the device and which rotates during injection may be monitored by a rotary position sensor whereby the dosing speed may be calculated from the rotary movement of the rotatably mounted component during injection.

EP1646844B2 discloses an injection device for administering and injectable drug, the device comprising a non-contact measuring unit for measuring a position between elements of a dosing device, and which can be moved relative to one another, the measuring unit comprising a magneto-resistive sensor, fixed to a first element, opposite a second magnetizable element, movable relative to the first element, and embodied as a rotational element for measuring rotational position; and a magnetic device formed from a permanent magnet on the first element, and a second magnetizable element with a predetermined surface profile such that when the first and second elements are moved relative to each other, a surface of the second element changes its distance from the permanent magnet of the first element, whereby a measurable change in resistance is generated in the magneto-resistive sensor due to the change in magnetic field. This is a fairly complex system with many additional moving parts built into the barrel, or body, of the injectable-drug delivery device, leading to a greater risk of potential failure of the various components, or potentially interfering interaction between the movements of the magnet and magnetizable elements, and the respective signals generated.

WO2013050535A2 discloses a system comprising a sensor assembly adapted to measure a magnetic field, and a moveable element adapted to be moved relative to the sensor assembly between two positions by a combined axial and rotational movement, the rotational movement having a pre-determined relationship to the axial movement. A magnet is mounted to the moveable element and configured to generate a spatial magnetic field which relative to the sensor assembly varies corresponding to both the axial and rotational movement of the magnet and thus the moveable element. A processor is configured to determine on the basis of measured values for the magnetic field an axial position of the moveable element. In this system, a magnetic field producing means is located on a longitudinal drive screw that is located within the body of the injectable-drug delivery device, and the sensors are located along a longitudinal axis of said drug delivery device. It is noted that the whole of this system is located once again within the main body of the drug delivery device, in order for the magnetic field to be generated as close as possible to the longitudinal axis along which the magnet moves, and the sensors.

WO2014161954A1 discloses a drug delivery system, wherein the housing of the drug delivery device further comprises, integrated inside said housing, a first rotational member adapted to rotate relative to the housing corresponding to a set and/or expelled dose and comprising a first force transmitting surface, a second rotational member adapted to rotate relative to the housing corresponding to a set and/or expelled dose and comprising a second force transmitting surface, wherein at least portions of the first and second force transmitting surfaces are adapted to engage each other during setting and/or expelling of a dose, wherein the first rotational member comprises a magnet producing a magnetic spatial field which varies corresponding to the rotational movement of the first rotational member, and wherein the first rotational member is fully formed from a polymeric material containing magnetic particles, the polymeric material having been magnetized to provide a magnet producing the magnetic spatial field.

All of the above solutions involve a fairly complex arrangement of various sensors and/or organisation of elements within the body of the drug delivery device, which moreover generally imply having to modify said drug delivery device fairly substantially.

WO2017013464A1 discloses a dose control device capable of functioning with a broad spectrum of currently available injectable-drug delivery devices, in which the dose control device is mounted at, or near the proximal extremity of an elongate body of a generally pen-shaped self-injection drug delivery device. In one embodiment, the dose control device comprises an annular component comprising a magnetic field producing means, such as a permanent dipole magnet, wherein said annular component is mounted at the proximal extremity of the elongate body on a known dose setting wheel commonly forming part of the injectable-drug delivery device, about the longitudinal axis of said elongate body, such that said annular component co-rotates with the dose setting wheel. Magnetic field detection means, connected to a signal processing unit, and located distally from said annular component, in a housing situated near the proximal extremity of the elongate body, serve to detect values of magnetic field for any angle of rotation of the annular component when the dose setting wheel is rotated. Such a dose control device does not require substantial modification of the injectable-drug delivery device or the way in which it functions for the user, i.e. its modus operandi, when compared to a like, off-the-shelf drug delivery device. Furthermore, such a device, being removably mounted on said injectable-drug delivery devices, enables the injectable-drug delivery devices to be exchanged, for example, in case of damage to the injectable-drug delivery device or malfunction in the injectable-drug delivery device, or simply because some injectable-drug delivery devices are configured to only deliver a small range of available doses of drug, requiring switching to another injectable-drug delivery device that has a different range of available doses of drug.

Despite the above progress, some currently available pen-type injectable-drug delivery devices function in a particular manner, in which rotational movement around, and/or translational movement along the longitudinal axis, of the magnetic field producing means, may or may not be desired and/or required. It is therefore an object of the present invention to provide a similar dose control device to the one described above, but which presents still yet more advantages and even greater flexibility and adaptability to the various use cases of the available pen-type injectable-drug delivery devices. These and other objects will become apparent from the various embodiments as indicated and detailed hereinafter.

As indicated above, this flexibility is particularly noteworthy in regard to movement of the annular component comprising the magnetic field producing means. The main issues can be summarized as follows:

1A) during a dose setting phase, i.e. at the time when a user sets the dose to be injected by rotating the dose setting wheel, the requirement for the magnetic field producing means to rotate both clockwise and counter-clockwise along with the dose setting wheel, and also translate in both a distal and proximal direction along with said dose setting wheel along the longitudinal axis of the drug delivery device;

1B) during a dose injection phase, ie. at the time when the drug is expelled, the requirement for the magnetic field producing means to not rotate in either the clockwise or anti-clockwise direction, and yet still be capable of moving only in a distal direction along the longitudinal axis of the drug delivery device;

2A) during a dose setting phase, the requirement for the magnetic field producing means to rotate both clockwise and counter-clockwise along with the dose setting wheel, and also to translate in both a distal and proximal direction along the longitudinal axis of the drug delivery device;

2B) during a dose injection phase, the requirement for the magnetic field producing means to rotate along with the dose setting wheel only in a single direction corresponding to a chosen dose, and yet still be capable of moving in a distal direction along the longitudinal axis of the drug delivery device;

3A) during a dose setting phase, the requirement for the magnetic field producing means to rotate both clockwise and counter-clockwise along with the dose setting wheel, and to forbid translational movement along the longitudinal axis of the drug delivery device in either a distal and proximal direction;

3B) during a dose injection phase, the requirement for the magnetic field producing means to rotate along with the dose setting wheel only in a single direction corresponding to a chosen dose, and yet still be capable of moving in a distal direction along the longitudinal axis of the drug delivery device.

Accordingly, one object of the present invention is a dose control device for a handheld pen-type injectable-drug delivery device, the handheld pen-type injectable-drug delivery device comprising an elongate body with a proximal and distal extremity, a longitudinal axis extending from the proximal extremity to the distal extremity, and a rotatable dose setting wheel located at the proximal extremity, wherein the dose control device comprises:

a magnetic field producing means located at the proximal extremity of said elongate body;

one or more magnetic field sensors in communication with a data processing unit located on an outer surface of, or inside, the elongate body; and a clutch assembly configured to selectively move the magnetic field producing means from a first, engaged, position, to a second, disengaged, position.

Various means for producing a magnetic field are known, for example, classical magnets, electromagnets, and mixed material magnets. Such magnets are typically made from magnetizable materials, having magnetic or paramagnetic properties, whether naturally or when an electric or other energizing flow traverses or affects said material to produce or induce a magnetic field in said material. Suitable materials can be appropriately selected from:

ferrite magnets, especially sintered ferrite magnets, for example, comprising a crystalline compound of iron, oxygen and strontium;

composite materials consisting of a thermoplastic matrix and isotropic neodymium-iron-boron powder;

composite materials made up of a thermoplastic matrix and strontium-based hard ferrite powder, whereby the resulting magnets can contain isotropic, i.e. non-oriented, or anisotropic, i.e. oriented ferrite particles;

composite materials made of a thermo-hardening plastic matrix and isotropic neodymium-iron-boron powder;

magnetic elastomers produced with, for example, heavily charged strontium ferrite powders mixed with synthetic rubber or PVC, and subsequently either extruded into the desired shape or calendered into fine sheets;

flexible calendered composites, generally having the appearance of a brown sheet, and more or less flexible depending on its thickness and its composition. These composites are never elastic like rubber, and tend to have a Shore Hardness in the range of 60 to 65 Shore D ANSI. Such composites are generally formed from a synthetic elastomer charged with strontium ferrite grains. The resulting magnets can be anisotropic or isotropic, the sheet varieties generally having a magnetic particle alignment due to calendaring;

laminated composites, generally comprising a flexible composite as above, co-laminated with a soft iron-pole plate;

neodymium-iron-boron magnets;

steels made of aluminium-nickel-cobalt alloy and magnetized;

alloys of samarium and cobalt.

Of the above list of magnetic field producing means suitable for use in the present invention, those selected from the group consisting of neodymium-iron-boron permanent magnets, magnetic elastomers, composite materials made up of a thermoplastic matrix and strontium-based hard ferrite powder, and composite materials made of a thermo-hardening plastic matrix and isotropic neodymium-iron-boron powder, are preferred. Such magnets are known for their ability to be dimensioned at relatively small sizes whilst maintaining relatively high magnetic field strength.

It is to be understood that the magnet is defined by a general disk shape, which could be circular, ellipsoid, or even any suitable polygonal shape, and has only a single dipole, in other words, a single pair of diametrically opposing north and south magnetic poles. As indicated above, although the magnet used in the present invention is substantially disk-shaped, such substantial disk-shape can also include magnets which have an orifice substantially in the centre of the disk to form a ring or annular shaped magnet.

The magnet of the present invention is configured to effect axial rotation around, and translate along, the longitudinal axis of the drug delivery system. The rotating displacement coincides with that of the dose setting wheel, meaning that turning or rotating the magnet around the longitudinal axis also causes said dose setting wheel to rotate in the same direction of rotation. Generally, the dose setting wheel is attached to a drive shaft or lead screw, which traverses an interior bore of the drug delivery device body. The dose control device can also calculate the distance of travel of the magnetic field producing means along the longitudinal axis.

In addition, the magnetic field producing means is dimensioned to provide sufficient magnetic field to be detected by the magnetic field sensors.

In the dose control system comprising the clutch assembly according to the present invention, at least a first and a second magnetic field sensors can be present and configured to measure the magnetic field produced by the magnet. The at least first and second magnetic field sensors are used to measure the magnetic field produced by rotational, and optionally translational, movement of the substantially disk-shaped magnet, to calculate an angular rotational position of the magnet in order to accurately determine which dose has been selected for administration via the injectable-drug delivery device. Optionally, and advantageously, such a system can also be used to calculate a translational position of a reference point of interest along the longitudinal axis of the drug delivery device body, which reference point can be used to correlate to a dose administered, a zero point, priming point, or initialization point for the system, a start point for injection, and/or an end point for injection.

Means for measuring magnetic fields to determine a rotational angular position are known generally in the art. For example, magneto-resistors are a well known means, some of which are used in the prior art systems. Such magneto-resistors are often designated by their abbreviations, e.g. AMR, GMR, TMR sensors, which designate the physical mechanisms by which these sensor components function. Giant magnetoresistance (GMR) is a quantum mechanical magnetoresistance effect observed in thin-film structures composed of alternating ferromagnetic and non-magnetic conductive layers. Anisotropic magnetoresistance, or AMR, is said to exist in materials in which a dependence of electrical resistance on the angle between the direction of electric current and direction of magnetization is observed. Tunnel magnetoresistance (TMR) is a magnetoresistive effect that occurs in a magnetic tunnel junction (MTJ), which is a component consisting of two ferromagnets separated by a thin insulator. Resistors that use these various properties are known per se.

In light of the above, the dose control device of the present invention preferably uses magnetometers, and preferably at least a first and second magnetometers, as the magnetic field sensors. These magnetometers differ from the GMR, AMR or TMR sensors in that they directly measure magnetic field strength. Magnetometers measure magnetic fields in two main ways: vector magnetometers measure the vector components of a magnetic field, and total field magnetometers or scalar magnetometers measure the magnitude of the vector magnetic field. Another type of magnetometer is the absolute magnetometer, which measures the absolute magnitude or vector magnetic field, using an internal calibration or known physical constants of the magnetic sensor. Relative magnetometers measure magnitude or vector magnetic field relative to a fixed but uncalibrated baseline, and are also called variometers, used to measure variations in magnetic field.

A preferred magnetometer for use in the dose control system according to the present invention is an ultra low-power high performance three axis Hall-effect magnetometer. Whilst it is possible for the magnetometer to be configured to measure magnetic field over three mutually perpendicular or orthogonal axes, it is nonetheless preferred that the magnetic field sensor be configured to measure magnetic fields over just two of the three orthogonal axes, for example the X and Z axes, whereby the Y axis is co-axial with the longitudinal axis of the drug delivery device body and thereby corresponds to the normal along which distance measurements relating to translational movement of the dose selector wheel along said longitudinal axis can be calculated as indicated above in respect to a reference point position on said axis.

The dose control device also advantageously comprises an integrated control and data processing unit connected to the magnetic field sensors for processing information received from the magnetic field sensors. This integrated control and data processing unit can be mounted, for example, on a printed circuit board of suitable dimensions to be located on, or within, the elongate body of the drug delivery device. The integrated control and data processing unit handles all electrical communication and signalling between the different electronic components of the dose control device. It is also responsible for execution of the dose management system and calculations enabling the precise positional location of the magnet to be calculated and determined, as well as handling signals from an autonomous power supply and communication means which communicate with a local or remote data processing system, e.g. on a smartphone. It can be programmed remotely, upon first use, or receive information and updates, in a similar way to other electronic devices today containing integrated control and data processing units. Such integrated control and data processing units are known per se, and often integrate a central processing unit, a real time clock, one or more memory storage systems, and optionally communications systems or subsystems, along with other desired components.

In one embodiment of the invention, the clutch assembly comprises:
- a cylindrical body having a longitudinal inner bore, wherein the magnetic field producing means is located within the bore of the cylindrical body, and the cylindrical body is removably mounted in axial longitudinal alignment around the rotatable dose setting wheel and rotatable therewith.

In another embodiment of the invention, the first, engaged position is a position in which the magnetic field producing means is held within the bore of the cylindrical body such that any rotational movement of the cylindrical body communicates directly to the magnetic field producing means causing the magnetic field producing means to rotate with the cylindrical body.

In yet another embodiment, the second, disengaged position is a position in which the magnetic field producing means is held within the bore of the cylindrical body such that any rotational movement of the cylindrical body is not communicated to the magnetic field producing means, thereby preventing the magnetic field producing means from rotating with the cylindrical body.

In another embodiment of the invention, the cylindrical body has a distal extremity, and the distal extremity is configured to mate with and grip an outer surface of the dose setting wheel.

In another embodiment of the invention, the cylindrical body has a proximal extremity, and the proximal extremity is configured to receive at least a part of a clutch activation button.

In another embodiment of the invention, the cylindrical body comprises a first annular wall extending within and along the bore towards the proximal extremity.

In a yet further embodiment of the invention, the first annular wall is connected to an inner surface wall of said cylindrical body.

In a yet further embodiment of the invention, the first annular wall is connected to the cylindrical body inner surface wall via a first annular skirt which extends radially outwards from the first annular wall to the cylindrical body inner surface wall.

In a yet further embodiment of the invention, the first annular wall, the first annular skirt and the cylindrical body inner surface wall form an annular groove for receiving at least a part of a clutch activation button.

In a yet further embodiment of the invention, the first annular wall further comprises a second annular skirt, located at a proximal extremity of the first annular wall, which projects radially inwardly from the first annular wall proximal extremity into the bore of the cylindrical body.

In a yet further embodiment of the invention, the annular wall further comprises at least one pair of clutch teeth projections, extending radially inwardly from an inner surface of the proximal extremity of the annular wall, into the bore of the cylindrical body.

In a yet further embodiment of the invention, the second annular skirt further comprises a second annular wall, extending from an inner extremity of the second annular skirt, wherein the second annular wall extends coaxially with the first annular wall towards the proximal extremity of the cylindrical body.

In a yet further embodiment of the invention, the second annular wall comprises at least one pair of clutch teeth projections, extending radially inwardly from an inner surface of the second annular wall, into the bore of the cylindrical body.

In a yet further embodiment of the invention, a distal extremity of each tooth projection of the at least one pair of clutch teeth projections has a cross-section and/or profile that is narrower than the cross-section of the tooth projection at a proximal end thereof.

In another embodiment of the invention, a distal extremity of each tooth projection of the at least one pair of clutch teeth projections is rounded.

In another embodiment of the invention, the clutch assembly further comprises a magnetic field producing means holder.

In a yet further embodiment of the invention, the magnetic field producing means holder comprises a holder body having a longitudinal bore, a proximal extremity and a distal extremity.

In a yet further embodiment of the invention, the magnetic field producing means holder body comprises a magnetic field producing means material.

In a yet further embodiment of the invention, the holder body comprises a skirt, located adjacent the distal extremity of the holder body, the skirt comprising a substantially planar surface extending radially outwards from the holder body and an annular peripheral wall extending distally from a peripheral edge of the substantially planar surface.

In a yet further embodiment of the invention, the skirt further comprises at least one seating means for the magnetic field producing means, located within an inner volume defined by the skirt, the seating means being configured to receive and seat the magnetic field producing means within the skirt.

In a yet further embodiment of the invention, the holder body further comprises an array of clutch teeth projections, extending radially outwards in spaced-apart relationship, from an outer, peripheral surface of the holder body, and located around the outer peripheral surface of the holder body.

In a yet further embodiment of the invention, the array of clutch teeth projections are selectively engageable with, and disengageable from, at least one pair of clutch teeth projections, extending radially inwardly from an inner surface of a proximal extremity of an annular wall of the cylindrical body.

In a yet further embodiment of the invention, the holder body further comprises an activation button engagement member, configured to engage and retain the clutch activation button.

In a yet further embodiment of the invention, the clutch activation button engagement member is located within the bore of the holder body, adjacent a proximal extremity thereof.

In another embodiment of the invention, the clutch assembly further comprises a clutch activation button.

In a yet further embodiment of the invention, the clutch activation button has a distal extremity comprising a distal surface, wherein in the clutch assembly disengaged position, the distal surface comes into contact with a corresponding proximal surface located at the proximal extremity of the cylindrical body, and in the clutch assembly engaged position, the distal surface of the proximal extremity of the clutch activation button is no longer in contact with the corresponding proximal surface located at the proximal extremity of the cylindrical body.

In a yet further embodiment of the invention, the clutch activation button comprises a button body, the button body extending from a proximal extremity towards a distal extremity of the button body, the button body comprising an annular wall projection extending distally along a longitudinal axis of the button body, wherein the annular wall projection has a diameter less than the diameter of the button body, thereby forming a distal shoulder at a spaced apart location from, and distal to, the proximal extremity of the button body, which said distal shoulder is dimensioned to come into contact with a corresponding proximal surface located at the proximal extremity of the cylindrical body in the clutch assembly disengaged position.

In a yet further embodiment of the invention, the annular wall of the activation button body has a distal extremity surface which, in the clutch assembly disengaged position, comes into contact with the annular groove formed by the first annular wall, first annular skirt and cylindrical body inner surface wall.

In a yet further embodiment of the invention, the annular wall projection of said activation button body defines an inner, substantially cylindrical volume inwardly of the annular wall projection, the inner volume having an open distal extremity and a closed proximal extremity.

In a yet further embodiment of the invention, the activation button comprises a holder engagement member, configured to retain and engage with an activation button engagement member provided on the magnetic field producing means holder.

In another embodiment of the invention, the clutch assembly further comprises a pre-constrained biasing member, located between an annular skirt projecting radially inwardly from an annular wall adjacent a proximal extremity of the cylindrical body, and a clutch activation button.

In a yet further embodiment of the invention, the pre-constrained biasing member is seated distally on the annular skirt of the annular wall of the cylindrical body, and inserted into an inner, substantially cylindrical volume of the activation button, to seat proximally against a closed proximal extremity of the inner volume.

In a yet further embodiment of the invention, the pre-constrained biasing member, in the disengaged clutch assembly position, adopts a relatively unconstrained conformation, and in the engaged clutch assembly position, a relatively constrained conformation.

In a yet further embodiment of the invention, the pre-constrained biasing member is compressed when in the disengaged clutch assembly position.

In a yet further embodiment of the invention, the pre-constrained biasing member is relaxed when in the engaged clutch assembly position.

In a yet further embodiment of the invention, the application of a force in a distal direction to the activation button causes compression of the pre-constrained biasing member, thereby causing the projecting teeth of the holder to disengage from biasing contact with corresponding projecting teeth of the cylindrical body and move the distal extremity surface of the clutch activation button annular wall into contact with the annular groove formed by the first annular wall, first annular skirt and cylindrical body inner surface wall.

In a yet further embodiment of the invention, the release of the compression on the pre-constrained biasing member causes the biasing member to expand to a relatively unconstrained, or relaxed, conformation, thereby causing the clutch activation button to move proximally and, due to the engagement connection between the holder engagement member and the activation button engagement member, causes the holder to also move proximally, bringing the projecting teeth of the holder to engage in biasing contact with corresponding projecting teeth of the cylindrical body.

In a yet further embodiment of the invention, the pre-constrained biasing member is a spring.

Insofar as the nature and type of the pre-constrained biasing member is concerned, a suitable choice can be made by the skilled person. However, for the purposes of the present invention, it has been found advantageous that the pre-constrained biasing member be a flat wire compression spring or a wave spring. Such flat wire compression springs, or wave springs are known generally in the art, and are available, for example, from the Smalley Steel Ring Company, under the CM and CMS range identifications, where CM refers to plain-ended wave springs, and CMS refers to shim-ended wave springs. Such springs are generally either made of carbon steel, or stainless steel.

In an alternative object of the invention, the dose control device has no interacting projecting teeth, but instead the cylindrical body further comprises a frictional layer located on an inner wall of the proximal extremity. The cylindrical body can be modified at its distal extremity through the provision of a friction layer as an alternative to the teethed engagement means, yet still enabling selectable engagement or disengagement between the magnetic field producing holder body and the clutch activation button. The frictional layer can be provided by any suitable material that provides sufficient friction engagement resistance to promote solidary co-rotational movement of the skirt surface of the magnetic field producing holder body with the cylindrical body when the skirt surface is engaged with the friction layer. Although a variety of suitable friction causing materials will enable such functionality, the applicants have found that a particularly suitable frictional engagement can be achieved when the friction layer comprises a relatively high shear coefficient polymeric material, for example having a Shore hardness of between 0 Shore A, with a consistency similar to a gel, and 70 Shore D, which in contrast is a relatively rigid material. Such polymers are known as thermoplastic elastomers, or TPEs for short, and are generally classified into 6 different families:

- styrene block copolymers, also known as TPS or TPE-s;
- thermoplastic polyolefin elastomers, also known as TPO or TPE-o;
- thermoplastic vulcanizates, also known as TPV or TPE-v;
- thermoplastic polyurethanes, also known as TPU;
- thermoplastic co-polyester, also known as TPC or TPE-E;
- thermoplastic polyamides, also known as TPA or TPE-a; and
- non-classified thermoplastic elastomers, also known as TPZ.

Whilst many of the above might be compatible with the envisaged functionality, the applicant has retained members from the styrene block copolymers, in particular materials made from or comprising polystyrene-b-poly(ethylene-butylene)-b-polystyrene, also known as SEBS polymers, and available for example under the brand name Kraton-G (Shell Chemicals), with a Shore A hardness of between about 40 and about 80, as the preferred material for the friction layer.

As mentioned above, the friction layer is advantageously located on an inner surface of the proximal extremity of the cylindrical body. In this regard, the friction layer can be a contiguous layer, a semi-contiguous layer, or be provided in the form of an array of deposits of the friction causing material, whereby any and each of these is adapted in thickness of layer or deposit to create the required friction effect. Preferably, the friction layer is an annular-shaped layer of SEBS material, which is furthermore seated on the inner surface of the proximal extremity of the cylindrical body via seating means. The seating means can for example be a sealant or an adhesive, disposed and or distributed on the inner surface and/or on a proximal surface of the friction layer that comes into contact with the inner surface. Preferably however, the applicant has found it advantageous to provide the seating means as dovetail extensions or projections of the friction material, which locate, and expand into, corresponding openings provided in the proximal extremity of the cylindrical body.

BRIEF DESCRIPTION OF THE FIGURES

The invention will now be described in more detail with regard to the accompanying figures, provided for the purpose of illustration and exemplification, in which.

DETAILED DESCRIPTION

Figure 1:
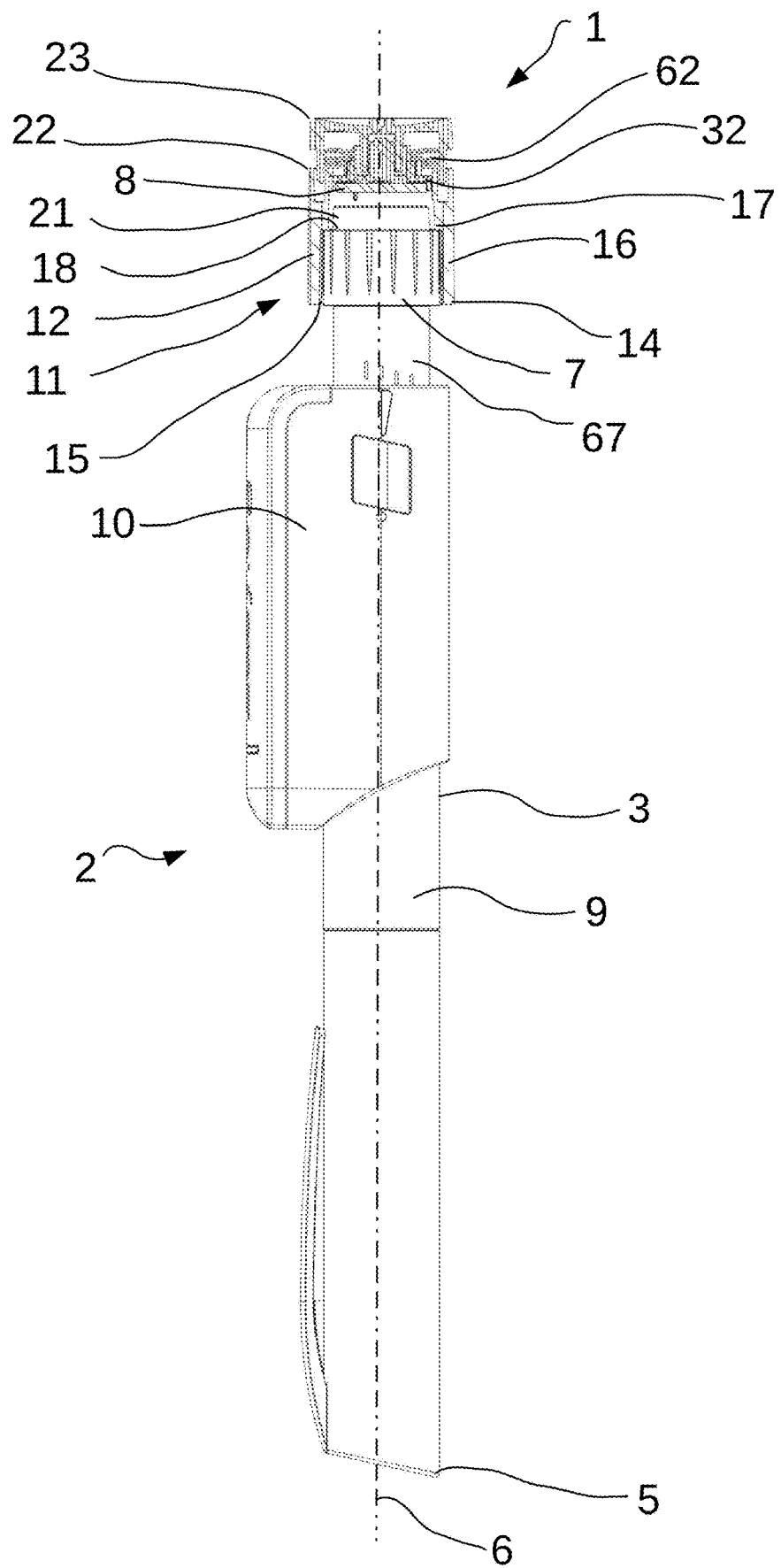
FIG. 1 is a schematic, cross-sectional representation of a dose control device according to the invention for a handheld pen-type injectable-drug delivery device.

The dose control device according to the invention will now be described in more detail with reference to the figures. In FIG. 1, a dose control device (1) for a handheld pen-type injectable-drug delivery device (2) is illustrated. The handheld pen-type injectable-drug delivery device, for example an auto-injector for the self-injection of drugs such as insulin, to name but one drug commonly administered in this way, comprises an elongate body (3) with a proximal (4) and distal extremity (5), a longitudinal axis (6) extending from the proximal extremity (4) to the distal extremity (5), and a rotatable dose setting wheel (7), as is commonly known from existing drug delivery devices such as auto-injectors, located at the proximal extremity (4). The dose setting wheel (7) also comprises a dose activation button (21), also commonly known from several auto-injector drug delivery devices. The dose activation button (21) serves to activate injection of the drug from the drug delivery device (2).

The dose control device generally comprises a magnetic field producing means (8) located at the proximal extremity (4) of said elongate body (3), one or more magnetic field sensors (not shown) in communication with a data processing unit (not shown) located on an outer surface (9) of, or inside, the elongate body (3). In FIG. 1, the magnetic field sensors and data processing unit are located within a housing (10) that is located on and around the outside surface (9) of the elongate body (3) of the drug delivery device (2), as exemplified and illustrated in the patent application published as WO2017013464A1. However, these sensors and data processing unit can also be directly integrated into the body (3) of the drug delivery device.

In addition to the general presentation of the dose control device as explained here, said dose control device is further defined by a clutch assembly (11) configured to selectively move the magnetic field producing means (8) from a first, engaged, position, to a second, disengaged, position. The clutch assembly comprises a cylindrical body (12) having a longitudinal inner bore (13), and the magnetic field producing means (8) is located within this bore (13). The cylindrical body (12) is removably mounted in axial longitudinal alignment with the longitudinal axis (6) around the rotatable dose setting wheel (7) and rotatable therewith. The first, engaged position is a position in which the magnetic field producing means (8) is held within the bore (13) of the cylindrical body (12) such that any rotational movement of the cylindrical body (12) communicates directly to the magnetic field producing means (8) causing the magnetic field producing means to rotate with the cylindrical body (12). This first, engaged position is illustrated in FIG. 2.

The second, disengaged position is a position in which the magnetic field producing means (8) is held within the bore (13) of the cylindrical body (12) such that any rotational movement of the cylindrical body (12) is not communicated to the magnetic field producing means (8), thereby preventing the magnetic field producing means (8) from rotating with the cylindrical body (12). This second, disengaged position is shown in FIG. 3.

Figure 2:
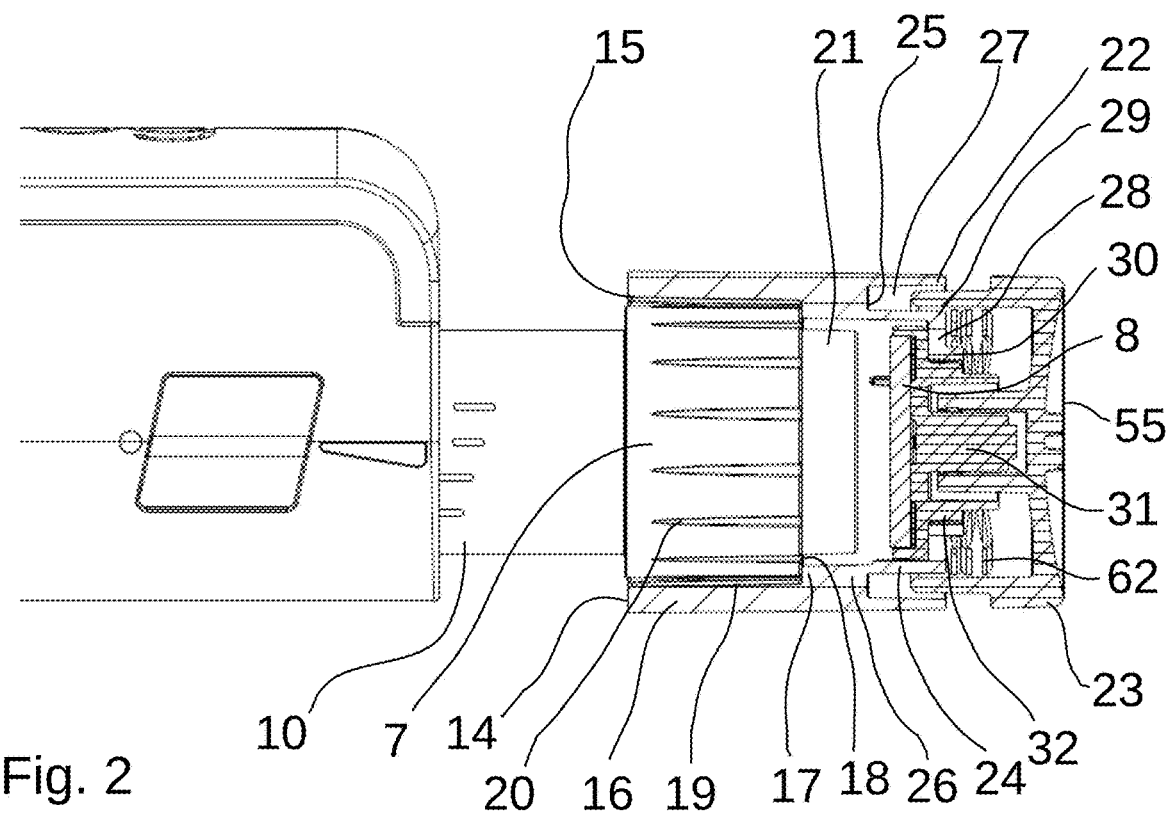
FIG. 2 is a schematic, cross-sectional close-up representation of the dose control device of FIG. 1, illustrating a clutch assembly of the dose control device in a first, engaged position.
Figure 3:
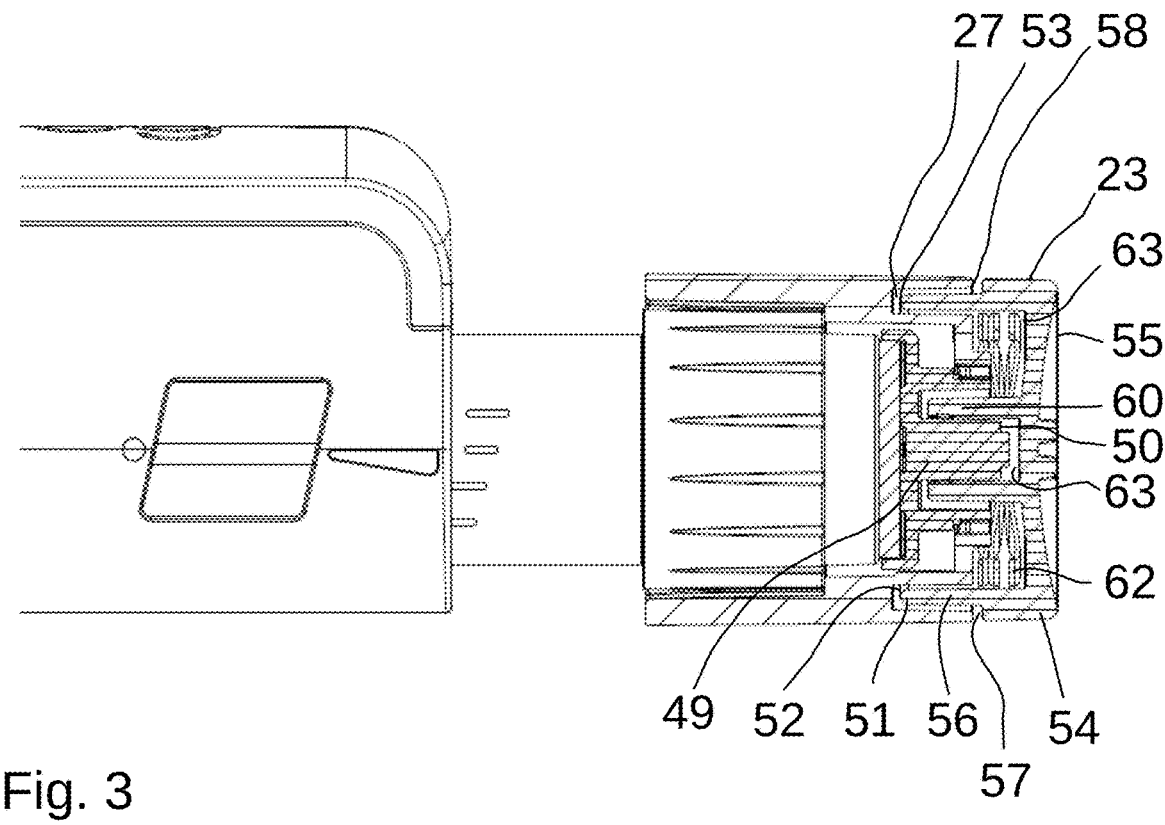
FIG. 3 is a schematic, cross-sectional close-up representation of the dose control device of FIG. 1, illustrating a clutch assembly of the dose control device in a second, disengaged position.
Figure 4:
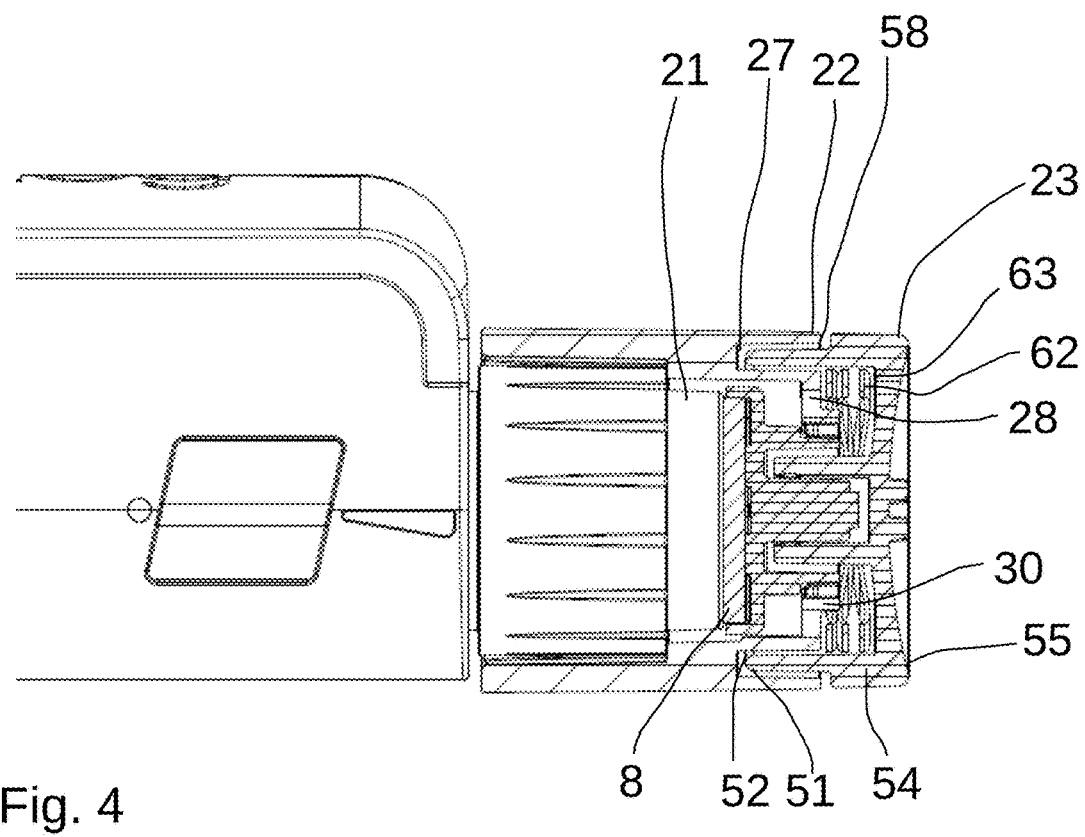
FIG. 4 is a schematic, cross-sectional close-up representation of the dose control device of FIG. 1, illustrating the relative position of the dose control device after activation of the injection step of the handheld pen-type injectable-drug delivery device.

FIGS. 2, 3 and 4 represent close-up views of a proximal part of the drug delivery device (2) and the detail of the dose control device (1).

The cylindrical body (12) has a distal extremity (14), which is configured to mate with and grip an outer surface (15) of the dose setting wheel (7) in a removable manner. As an example of a suitable configuration which enables this, the cylindrical body (12) can be shaped, at its distal extremity (14) to form an elastically engaging wall (16), which wall can have an internal diameter or bore that is slightly smaller than the corresponding outer diameter of the dose setting wheel (7), and an internal annular shoulder (17) provided at a location proximally distant from the distal extremity (14). In this way, when the cylindrical body (12) is inserted onto and around the dose setting wheel (7), it does so in increasingly elastic engagement caused by increased friction between an inner surface (19) of said wall (16) and said outer surface (15) of the dose setting wheel (7), until the shoulder (17) comes into engaging abutment with a proximal surface (18) of the dose setting wheel (7).

Alternatively, the inner surface of the wall can comprise projecting lugs which project inwards into the bore and onto the outer surface of the dose setting wheel. In a like and corresponding manner, the outer surface of the dose setting wheel can be provided with corresponding mating grooves (20), or pockets, for example, extending in spaced apart relationship around the outer surface (15) of said dose setting wheel (7), in a longitudinal direction along said longitudinal axis (6) or in an otherwise functionally equivalent manner.

The cylindrical body (12) is thus held tightly, but removably, onto the dose setting wheel (7), with the result that when the dose setting wheel (7) is rotated, the cylindrical body (12) also rotates to the same extent, or vice-versa, i.e. when the cylindrical body (12) is rotated, such rotation is imparted also to the same extent to the dose setting wheel (7), thereby allowing a user to set the dose to be administered by the drug delivery device, and not impede the usual modus operandi of said drug delivery device.

The cylindrical body (12) also has a proximal extremity (22), which is configured to receive at least a part of a clutch activation button (23). Reception of the clutch activation button (23) can be achieved by providing a first annular wall (24) at the proximal extremity (22) of the cylindrical body (12), which first annular wall (24) extends within and along the bore (13) towards the proximal extremity (22). The first annular wall (24) is connected to and bears onto an inner surface wall (15) of said cylindrical body (12), for example, via a first annular skirt (25) which extends radially outwards from the first annular wall (24) to the cylindrical body inner surface wall (15), or alternatively and/or additionally, via a thickened portion (26) of said inner surface wall (15). In this way, the first annular skirt (25) and the cylindrical body inner surface wall (15) form an annular groove (27) for receiving at least a distal part of the clutch activation button (23).

Additionally, the first annular wall (24) further comprises a second annular skirt (28), located at a proximal extremity (29) of the first annular wall (24), which projects radially inwardly from the first annular wall proximal extremity (29) into the bore (13) of the cylindrical body (12). The second annular skirt (28) further comprises a second annular wall (30), extending from an inner extremity of the second annular skirt (28), and wherein the second annular wall (30) extends coaxially with the first annular wall towards the proximal extremity (22) of the cylindrical body (12).

Figure 5:
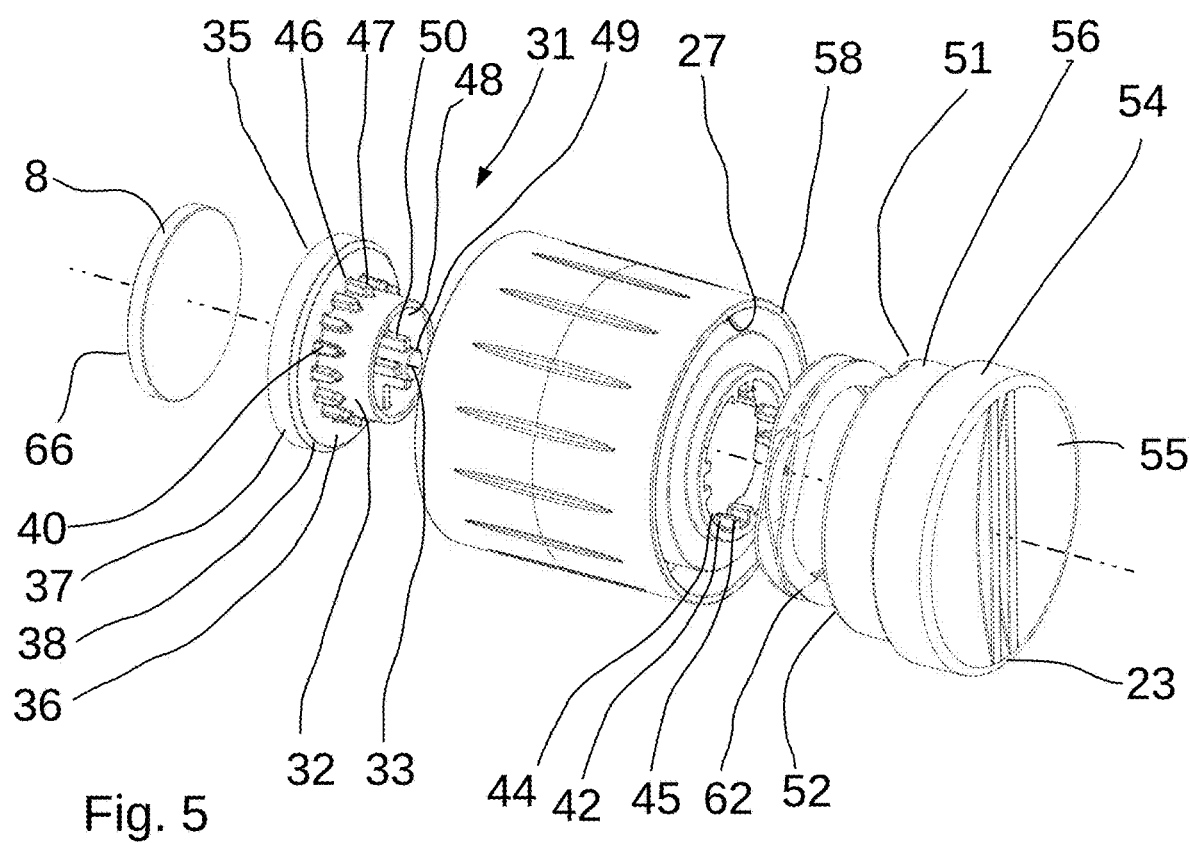
FIG. 5 is a schematic, exploded view of a dose control device according to the present invention, along a line of sight from a proximal extremity of said device towards a distal extremity of said device.
Figure 6:
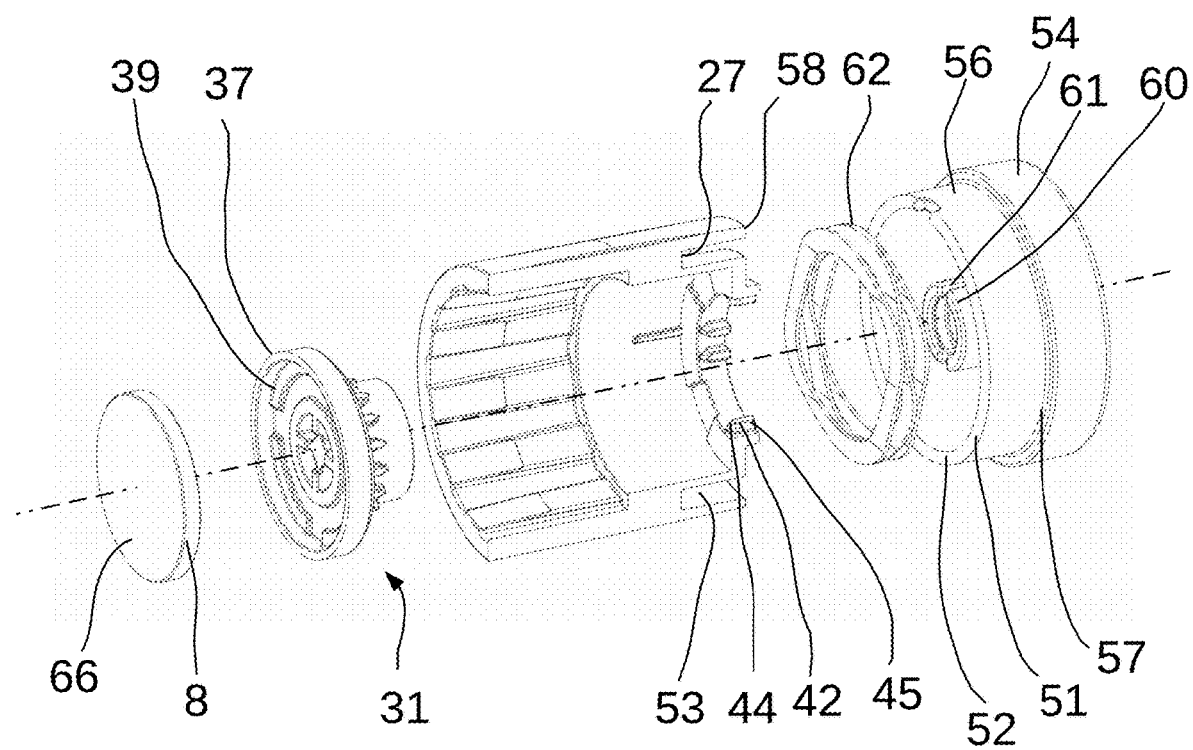
FIG. 6 is a schematic, exploded view of a dose control device according to the present invention, along a line of sight from a distal extremity of said device towards a distal extremity of said device.

As illustrated in more detail in the exploded views of FIGS. 5 and 6, the clutch assembly (11) further comprises a magnetic field producing means holder (31), comprising a holder body (32) having a longitudinal bore (33), a proximal extremity (34) and a distal extremity (35). The magnetic field producing means holder (30) is located within the bore (13) of the cylindrical body (12) and is configured to either hold or seat the magnetic field producing means (8), or otherwise be comprised at least partly of magnetic field producing means material. As illustrated by the figures, the magnetic field producing means (8) is a disk, preferably a disk-shaped dipole magnet (8) having only a single north and south pole arranged in diametrically opposite fashion, wherein one half of the disk is the north pole and the other half of the disk is the south pole. Alternatively, the magnetic means producing holder body (32) can be constituted at least partly by a magnetic field producing means material, such as, for example, a known suitable plasto-magnetic material, which is generally comprised of a heat-formable or heat-shapable plastic in which magnetic or magnetizable particles have been embedded or distributed. In the figures, the holder body (32) comprises a skirt (36), located adjacent the distal extremity (35) of the holder body (32), the skirt (36) comprising a substantially planar surface extending radially outwards from the holder body (32) and an annular peripheral wall (37) extending distally from a peripheral edge (38) of the substantially planar surface.

The skirt (36) of the magnetic field producing means holder body (32) further comprises at least one seating or locating means (39) for the magnetic field producing means (8), the seating or locating means being disposed within an inner volume defined by the skirt (36), and being configured to receive and seat the magnetic field producing means (8) within the skirt (36). In FIGS. 5 and 6, the seating means (39) comprises one or more raised or projecting edges located around an inner periphery of the inner volume of the skirt (36) into which, or alternatively, onto which, the magnetic field producing means (8) is either inserted or secured, for example by elastic engagement with said seating or locating means (39) and an outer peripheral surface of the disk-shaped magnetic field producing means (8).

The holder body (32) further comprises an array of clutch teeth projections (40), extending radially outwards in spaced-apart relationship, from an outer, peripheral surface (41) of the holder body (32), and located around said outer peripheral surface (41) of the holder body (32). This array of clutch teeth projections (40) is selectively engageable with, and disengageable from, at least one corresponding pair of clutch teeth projections (42), extending radially inwardly from an inner surface (43) of a proximal extremity (44) of the second annular wall projecting inwardly from the first annular wall and connected to the cylindrical body (12). A distal extremity (44) of each tooth projection (42) of the at least one pair of clutch teeth projections (42) has a cross-section and/or profile that is narrower than the cross-section of the tooth projection (42) at a proximal end (45) thereof. Preferably, said distal extremity of each tooth projection (42) of the at least one pair of clutch teeth projections (40) is rounded. In a similar, but opposite manner, the clutch teeth projections (40) of the magnetic field producing means holder body (32) have a proximal (46) and distal (47) extremity. The proximal extremity (46) of the clutch teeth projections (40) of the magnetic field producing means holder body (32) has a cross-section and/or profile that is narrower than the cross-section of the same tooth projection (40) at a distal end (47) thereof. This arrangement facilitates cooperative sliding engagement and disengagement of the various teeth projections (40, 42) in the eventuality of partial axial misalignment of the holder teeth (40) with the cylindrical body teeth (42), for example, which might occur after the clutch assembly has been activated to move the magnetic field producing means from a first, engaged, position, to a second, disengaged, position, and then re-activated to move the magnetic field producing means from the second, disengaged, position, back into the first, engaged position.

The holder body (32) also comprises a clutch activation button engagement member (48), configured to engage and retain the clutch activation button (23). As illustrated in FIG. 5, this engagement member (48) is provided by a projection extending in a proximal direction towards the proximal extremity of the holder (34) and internally within the bore (33) of the holder body (32), away from the holder skirt (36). In FIG. 5, the clutch activation button engagement member (48) is presented as having a substantially cross-shaped cross-section, with a cylindrical rod-like projection (49) in the centre and directed along the longitudinal axis (6), from which four equally spaced apart block-like projections (50) extend radially outwards into the bore (33).

As been mentioned above, the clutch assembly further comprises a clutch activation button (23). The clutch activation button has a distal extremity (51) comprising a distal surface (52), and the distal surface (52) comes into contact with a corresponding proximal surface (53) located adjacent the proximal extremity (22) of the cylindrical body (12), when the clutch assembly is in the disengaged position. When the clutch assembly is in the engaged position, the distal surface (52) of the distal extremity (51) of the clutch activation button (23) is no longer in contact with the corresponding proximal extremity surface (53) located at the proximal extremity of the cylindrical body. The clutch activation button also comprises a button body (54), the button body extending from a proximal extremity (55) of the clutch activation button (23) towards a distal extremity (51) of the button body, and comprising an annular wall (56) extending distally along a longitudinal axis of the button body (54). The button body annular wall (56) has a diameter less than the diameter of the button body (54), thereby forming a distal shoulder (57) at a spaced apart location from, and distal to, the proximal extremity (55) of the button body (54). This distal shoulder (57) is dimensioned to come into contact with a corresponding proximal surface (58) located at the proximal extremity (22) of the cylindrical body (12), when the clutch assembly (11) is in the disengaged position. When the clutch assembly is in the engaged position, however, the distal shoulder (57) and the proximal surface (58) are not in contact with each other, leaving a gap between the two. The annular wall (56) of the activation button body (54) has a distal extremity surface (52) which, in the clutch assembly disengaged position, comes into contact with the annular groove (27) formed by the first annular wall (24), first annular skirt (25) and cylindrical body inner surface wall (15). The annular wall (56) of the clutch activation button body (54) also defines an inner, substantially cylindrical volume inwardly of the annular wall (56), with the inner volume having an open distal extremity (59) and a closed proximal extremity (63). A holder engagement member (60), is located within the inner volume, and as illustrated comprises a cleft cylindrical projection (61), extending from the closed proximal extremity (63) towards the open distal extremity (59) of said inner volume, the cleft cylindrical projection (61) being shaped and dimensioned to retain, surround and engage with the cylindrical rod-like projection (49) and at least some of the four equally spaced apart block-like projections (50) of the activation button engagement member (48) provided on the magnetic field producing means holder (31).

As can also be seen from the figures, the clutch assembly (11) further comprises a pre-constrained biasing member (62), located between the second annular skirt (28) projecting radially inwardly from the first annular wall (24) adjacent the proximal extremity (22) of the cylindrical body (12), and the clutch activation button (23). As shown in the figures, the pre-constrained biasing member (62) is seated distally on the second annular skirt (28) of the first annular wall of the cylindrical body (12). The pre-constrained biasing member is also located around, and can be relaxed and be compressed, along and around the second annular wall (30). At the same time, the pre-constrained biasing member (62) is inserted into and housed by, the inner, substantially cylindrical volume of the clutch activation button (23), to seat proximally against the closed proximal extremity (63) of the inner volume. This arrangement can be clearly seen in FIGS. 3 and 4. In the disengaged clutch assembly position, the pre-constrained biasing member (62) adopts a relatively constrained or compressed conformation, for example, as illustrated in FIG. 3, and in the engaged clutch assembly position, a relatively unconstrained or relaxed conformation, as illustrated in FIG. 2.

The functioning of the clutch assembly can be summarised as follows:
  application of a force, for example a push of the user's thumb or finger, on the clutch activation button (23), in a distal direction causes compression of the pre-constrained biasing member (62), thereby causing the projecting teeth (40) of the holder (31) to disengage from biasing contact with the corresponding projecting teeth (42) of the cylindrical body (12). At the same time, the distal extremity surface (52) of the clutch activation button body annular wall comes into contact with the annular groove (27) formed by the first annular wall (26), first annular skirt (28) and cylindrical body inner surface wall (15);
  release of the compression force on the pre-constrained biasing member (62), for example by relaxing the thumb or finger pressure that was being exerted in the distal direction by the user, causes the biasing member (62) to expand, or decompress to a relatively unconstrained, or relaxed, conformation, thereby causing the clutch activation button (23) to move proximally. As the engagement connection between the holder engagement member (48) and the clutch activation button engagement member (60) holds both members together, the proximal movement of the clutch activation button (23) causes the holder to also move in a proximal direction, thereby bringing the projecting teeth (40) of the holder (31) to engage once more in biasing contact with the corresponding projecting teeth (42) of the cylindrical body (12). A suitable pre-constrained biasing member for use in the present device is a spring, and preferably a flat wire compression spring or a wave spring. Flat wire compression springs are particularly advantageous in the present invention because they enable the development of a sufficient range of compression and relaxation along a short distance for relatively very small diameters.

In use, the dose control device equipped with a clutch assembly functions as follows:

FIG. 2 shows the clutch assembly (11) in a pre-mounted and ready to use state, typically as would be found when a user removes the drug delivery device (2) from its packaging. Mounting of the clutch assembly (11) to the dose setting wheel (7) would generally occur during packaging of the drug delivery device, for example, at the production site of said drug delivery device (2). However, as the clutch assembly (11) is also removable, it can be removed after use, and disposal, of the drug delivery device, for example for recycling. Alternatively, the clutch assembly could also be mounted by the user when preparing the drug delivery device for use, along with any other mountable components of the dose control device, such as the one or more magnetic field sensors in communication with a data processing unit as described in WO2017013464A1. Whatever the case, as illustrated in FIG. 2, the clutch assembly is mounted onto and around the dose setting wheel (7). The cylindrical body extends, from a distal extremity (14) towards a proximal extremity (22), whereby the distal extremity (14) is in substantial alignment with the distal extremity of the dose setting wheel (7). The cylindrical body (12) therefore extends, when mounted on the drug delivery device (2), from the distal extremity (64) of the dose setting wheel, in a proximal direction to beyond the proximal extremity (65) of said dose setting wheel (7), which proximal extremity (65) has an exposed proximal surface (18), with which the shoulder (17) of the cylindrical body is in engaging abutment. A drug delivery, injection, or dose activation, button (21) is located and in contact with the dose setting wheel (7) and forms an integral part of the drug delivery device (2). Adjacent the proximal extremity (22) of the cylindrical body, the clutch activation button (23) and magnetic field holder (31) engage, via respective engagement members (48, 60) with each other, the magnetic field holder (31) being retained by the clutch activation button (23). The pre-constrained biasing member (62), in this case a flat wire compression spring, is seated distally on the proximal surface of the second annular skirt (28), about and around the second annular wall (30), in a relatively unconstrained or relaxed conformation. Although not shown in FIG. 2, the spring extends in a proximal direction in the unconstrained or relaxed conformation all the way along to seat on, or abut against, the inner volume proximal extremity (63). As can be seen from FIG. 2, the holder (31) is pulled by the pre-constraint imparted to the spring (62), in its unconstrained or relaxed conformation, via the engagement connection (48, 60) of the holder to the clutch activation button (23), such that the projection teeth (40) of the holder (31) engage with the projection teeth (42) of the cylindrical body. The distal face (52) of the button body (54) remains within the annular groove (27), and is located adjacent a proximal extremity thereof and adjacent the proximal extremity (22) of the cylindrical body (12). This represents the first, engaged position, as any rotational movement imparted to the cylindrical body (12) is also directly communicated via reciprocal engagement of the respective engagement teeth (40, 42) to the magnet (8). Rotation of the magnet (8) causes a change in the distribution of magnetic field components produced in three dimensions about the axis of rotation of the magnet, and which coincides with the longitudinal axis (6) of the drug delivery device (2), and these changes are detected by the magnetic field sensors located on or in the drug delivery device body. Rotation of the dose wheel also sets the dose of unit drug to be administered via the drug delivery device in a known manner. Once the desired dose has been set, the user presses on the clutch activation button proximal extremity (55) with a thumb or finger to move the clutch assembly in distal direction into the disengaged position. In the disengaged position, as can be seen from FIG. 3, the clutch activation button (23) has been pressed by the user. The button moves against, and compresses the pre-constrained biasing member (62), moving the spring from a relaxed, or unconstrained conformation to a compressed, or constrained conformation. As this occurs, the distal surface (52) of button body (54) moves deeper into the annular groove so that the distal surface (52) finally comes into engaging abutment, or near engaging abutment with the proximal surface of the first annular skirt (25) of the cylindrical body (12). Likewise, the distal shoulder (57) of the button body (54) comes into surface engaging abutment with the proximal surface (58) located at the proximal extremity (22) of the cylindrical body (12). During the distal movement, projecting teeth (40) of the holder (31) are pushed out of engaging and abutting contact with the projecting teeth (42) of the cylindrical body (12), but still remain connected to the clutch activation button via the respective and corresponding engagement members (48, 60). This position is the second, disengaged position. For as long as the finger or thumb pressure is maintained in the distal direction by the user on the clutch activation button, the second, disengaged position will be enforced. One will also note that in the disengaged position, the magnet (8), being free of any engaging abutment between the projecting teeth (40, 42), is now no longer affected by any rotational movement applied to the cylindrical body, and it is possible to rotate the cylinder body, and corresponding dose setting wheel, if so desired, without impacting on the three-dimensional magnetic field components generated by the magnet (8). Note also that in the disengaged position, the distal surface (66) of the magnet (8) is in contact with, or very close proximity to, the proximal surface of the drug delivery activation button (21). Consequently, it now becomes possible to activate the drug delivery within the drug delivery device by continuing to apply a distally oriented pressure on the clutch activation button (23). This distally oriented pressure will cause the clutch assembly to move in a distal direction, with the magnet's (8) distal surface (66) bearing on the drug delivery activation button (21). As said drug delivery activation button (21) is in contact with the dose setting wheel (7), and the injection barrel (67) of the drug delivery device, these elements are also moved forward in a distal direction to effect injection and delivery of the drug from the drug delivery device. The final position of the clutch assembly (11), dose setting wheel and drug delivery activation button (21) at the end of the injection step are illustrated in FIG. 4. After injection has completed, pressure on the clutch activation button (23) is released or relinquished, and the pre-constrained biasing member (62) will bias the clutch activation button and connected holder (31) back in the proximal direction, bringing with it the holder (31), along with corresponding projecting teeth (40) and moving the clutch assembly (11) back into the first, engaged position, where the respective projecting teeth (40, 42) are once again in abutting engagement with each other. Rotation of the cylindrical body, will once again cause the magnet (8) to rotate, allowing the dose setting wheel to be used for further preparation of the administration of drug.

Turning now to FIGS. 7, 8, 9, 10 and 11, a dose control device according to the invention is illustrated comprising an alternative clutch assembly as will be described hereinafter. Like reference numerals will be used with reference to like elements of the device.

Figure 7:
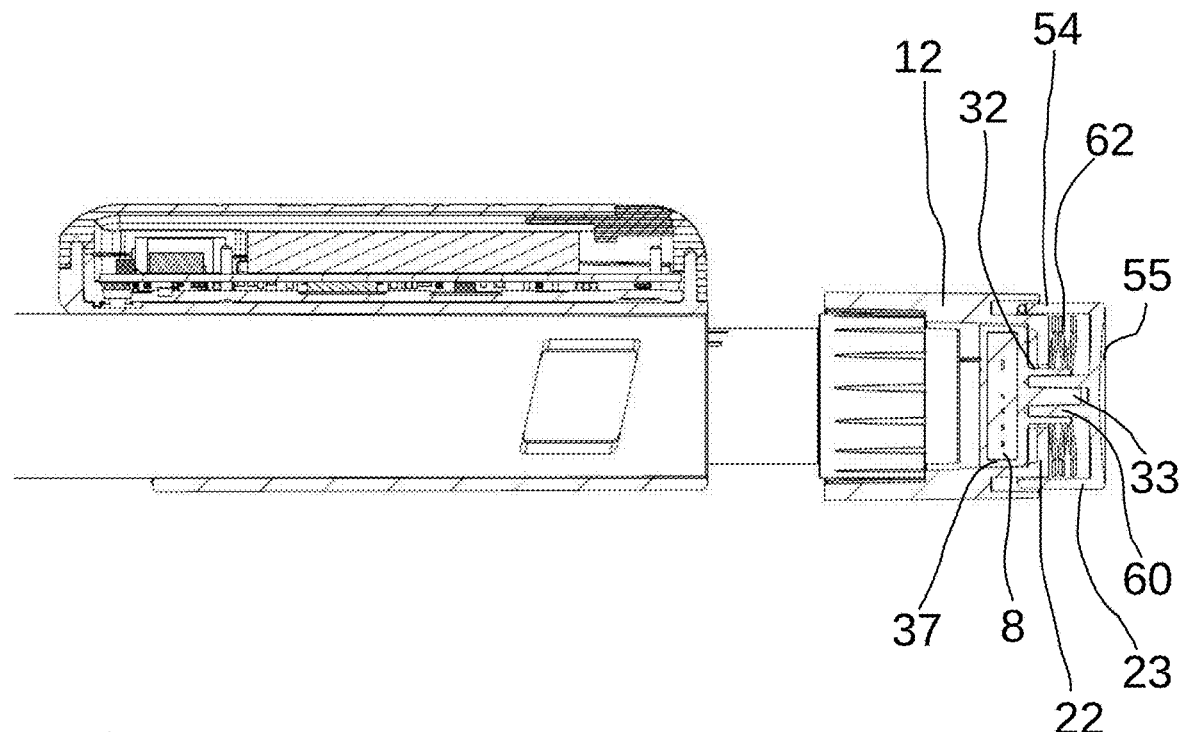
FIG. 7 is a schematic, cross-sectional close-up representation of a dose control device according to the present invention similar to that represented in FIG. 2 with a different clutch assembly in a first, engaged position.

FIG. 7 shows this alternative clutch assembly mounted with cylindrical body (12) in an engaged position in which spring (62) is in a relaxed or substantially unconstrained conformation similar to FIG. 2. In such a position, the spring (62) biases the clutch activation button (23) away from the cylindrical body in a proximal direction along the longitudinal axis (6) of the dose control device (1). The clutch activation button (23) has a distal extremity (51) comprising a distal surface (52), as in FIG. 2. When the clutch assembly is in the engaged position, the distal surface (52) of the distal extremity (51) of the clutch activation button (23) is not in contact with the corresponding proximal extremity surface (53) located at the proximal extremity (22) of the cylindrical body (12). The clutch activation button (23) also comprises a button body (54), the button body extending from a proximal extremity (55) of the clutch activation button (23) towards a distal extremity (51) of the button body (54), and comprising an annular wall extending distally along a longitudinal axis of the button body (54), which is in co-axial alignment with the longitudinal axis (6). This is the default resting position of the clutch assembly, for example, before the device is used to administer an injection, or alternatively, when a user of the drug delivery device has carried out an injection. In this alternative embodiment of the clutch assembly, there are no interacting sets of engagement teeth provided on the magnetic field producing body (31) on the one hand, and on the cylindrical body on the other hand. Instead, the engagement means are provided by a friction layer (68) located on an inner surface (69) of the proximal extremity (22) of the cylindrical body (12) as will be described in more detail hereafter with regard to FIGS. 10 and 11.

Figure 8:
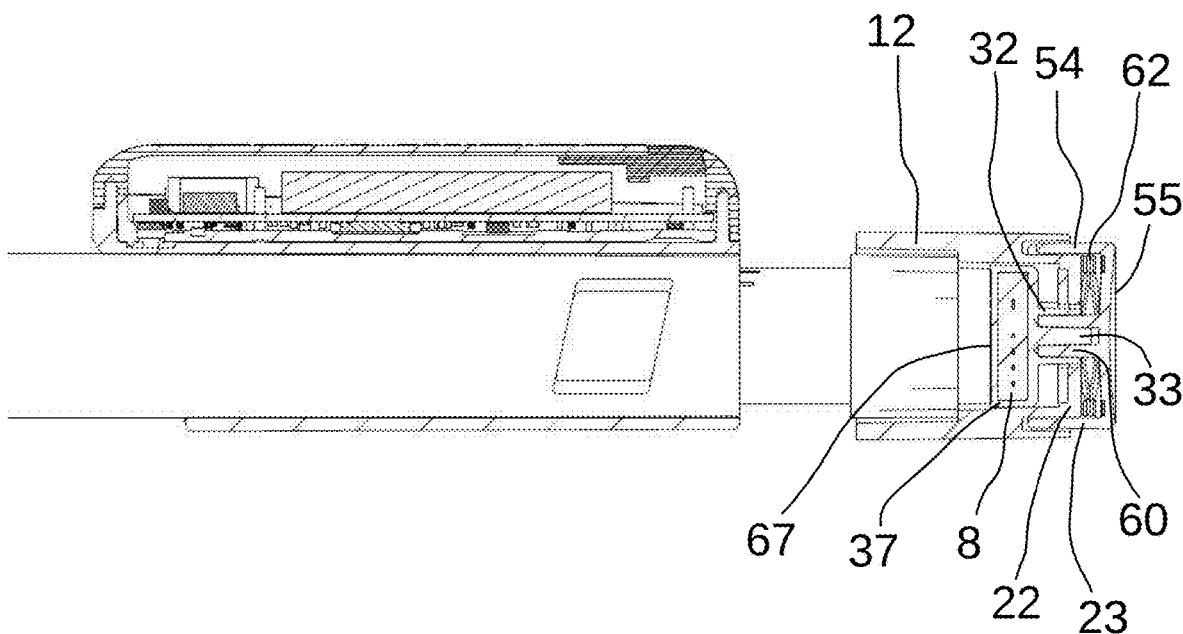
FIG. 8 is a schematic, cross-sectional close-up representation of the dose control device of FIG. 7, illustrating a clutch assembly of the dose control device in a second, disengaged position.
Figure 9:
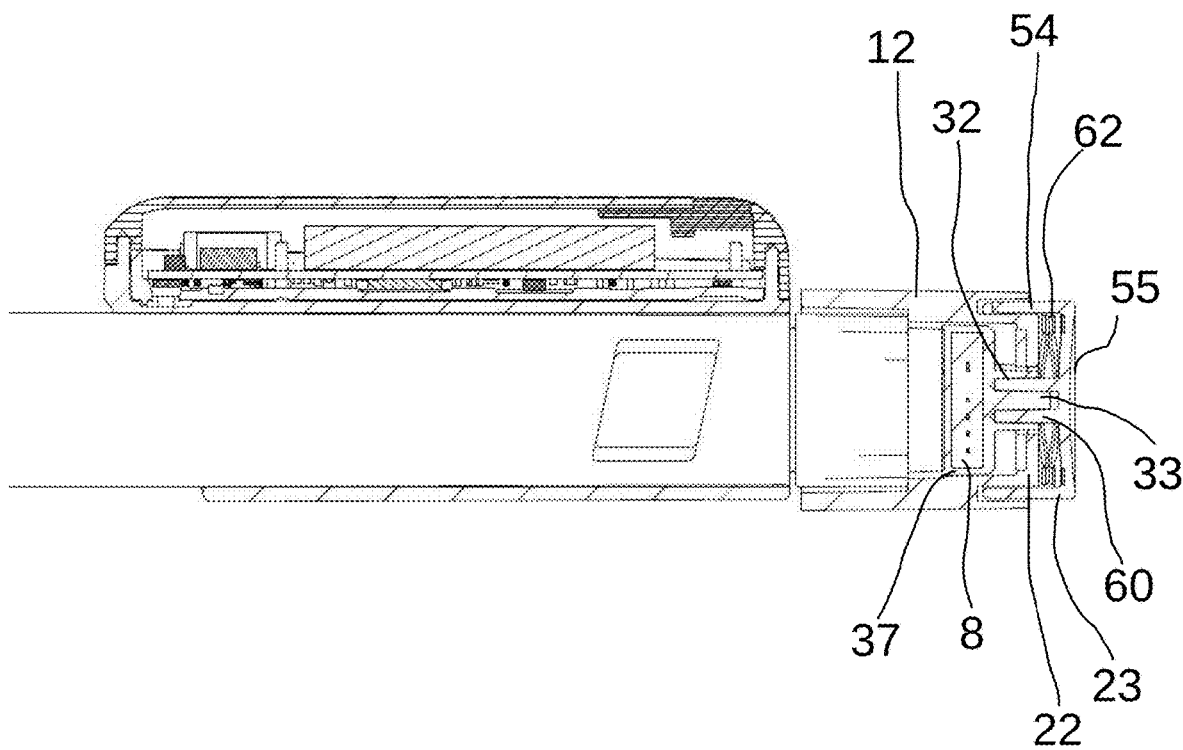
FIG. 9 is a schematic, cross-sectional close-up representation of the dose control device of FIG. 7, illustrating the relative position of the dose control device after activation of the injection step of the handheld pen-type injectable-drug delivery device.

FIG. 8 shows the relative positions of the clutch assembly and dose control device when the clutch assembly is in the disengaged position, in which the user is preparing the drug delivery device for an injection. In this position, the spring (62) is in a compressed or substantially constrained conformation, and the distal surface (52) of the distal extremity (51) button body (54) comes into contact with a corresponding proximal surface (53) located adjacent the proximal extremity (22) of the cylindrical body (12). For as long as the finger or thumb pressure is maintained in the distal direction by the user on the clutch activation button, the second, disengaged position will be enforced. One will also note that in the disengaged position, the magnet (8), being free of any engaging abutment between the projecting teeth (40, 42), is now no longer affected by any rotational movement applied to the cylindrical body, and it is possible to rotate the cylinder body, and corresponding dose setting wheel, if so desired, without impacting on the three-dimensional magnetic field components generated by the magnet (8). Note also that in the disengaged position, the magnet (8) is in contact with, or very close proximity to, the proximal surface of the drug delivery activation button (21). Consequently, it now becomes possible to activate the drug delivery within the drug delivery device by continuing to apply a distally oriented pressure on the clutch activation button (23). This distally oriented pressure will cause the clutch assembly to move in a distal direction, with the magnet's (8) distal surface (66) bearing on the drug delivery activation button (21). As said drug delivery activation button (21) is in contact with the dose setting wheel (7), and the injection barrel (67) of the drug delivery device, these elements are also moved forward in a distal direction to effect injection and delivery of the drug from the drug delivery device. Accordingly, FIG. 9 shows the relative positions of the clutch assembly and dose control device after the user has effected such an injection.

Figure 10:
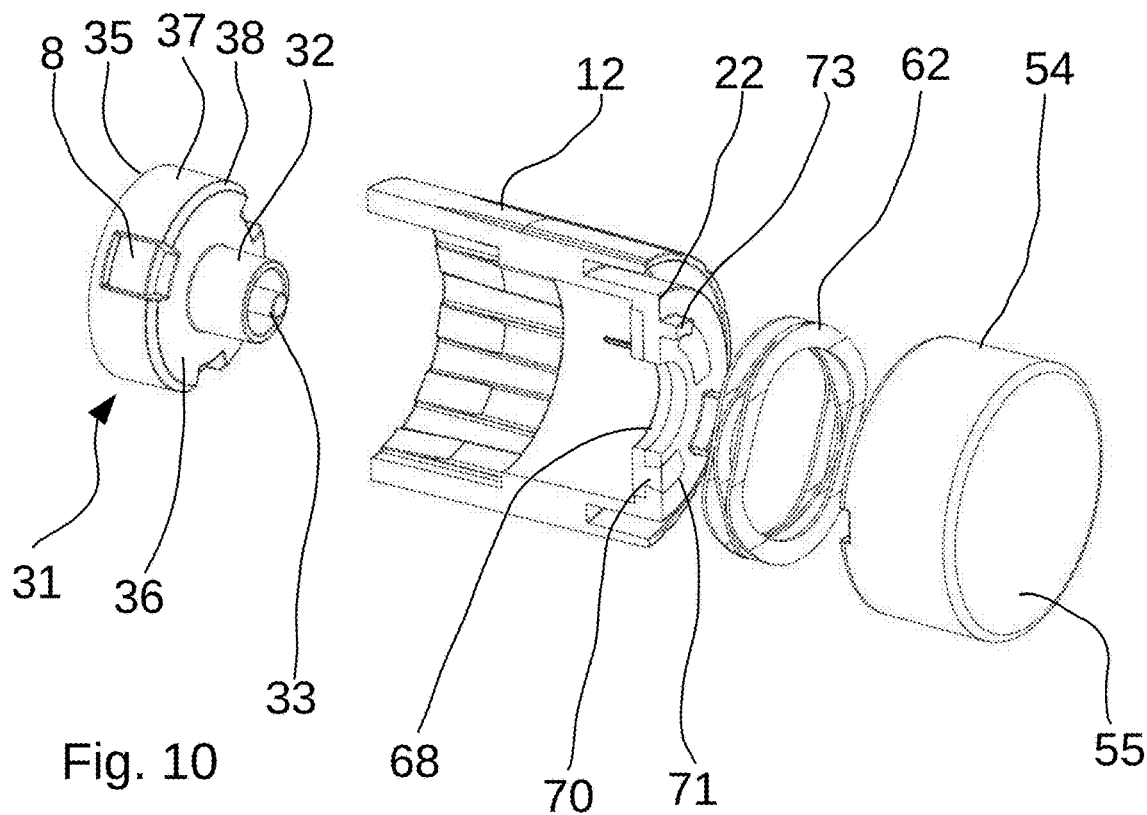
FIG. 10 is a schematic, exploded view of a dose control device according to the present invention with the alternative clutch assembly of FIG. 7, along a line of sight from a proximal extremity of said device towards a distal extremity of said device.
Figure 11:
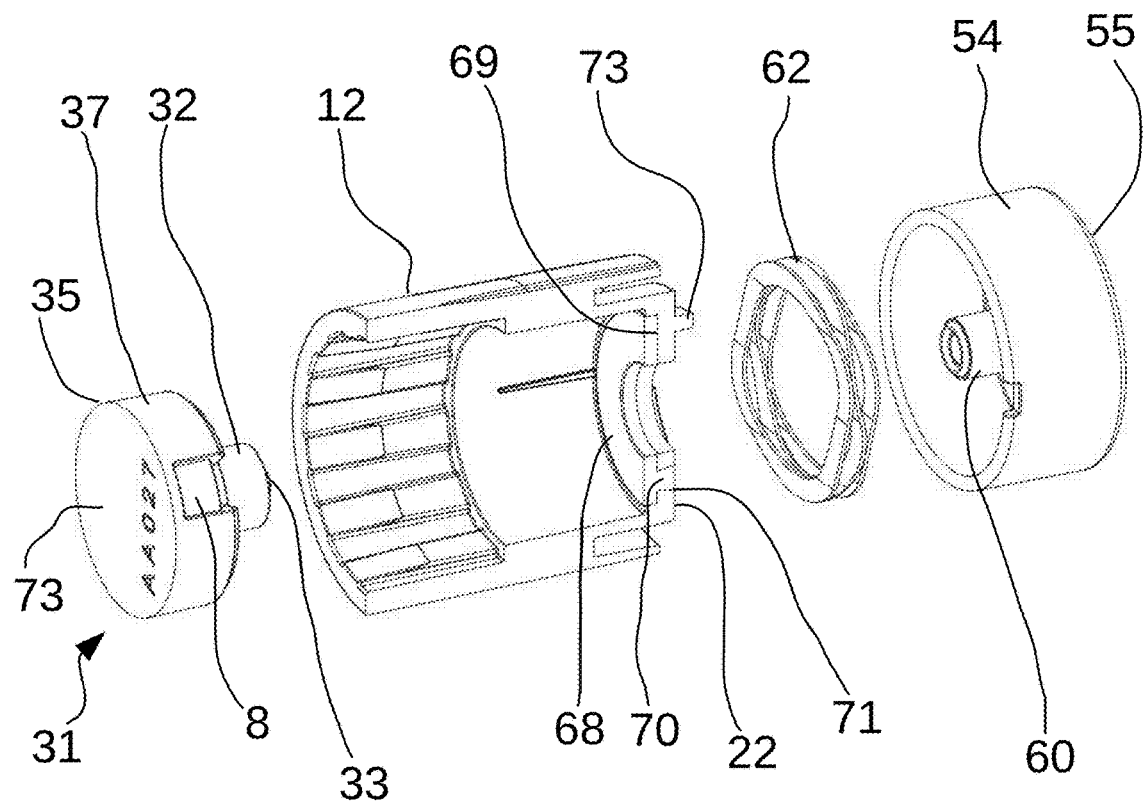
FIG. 11 a schematic, exploded view of a dose control device according to the present invention with the alternative clutch assembly of FIG. 7, along a line of sight from a distal extremity of said device towards a distal extremity of said device.

FIGS. 10 and 11 represent schematic exploded and more detailed perspective views of the alternative clutch assembly along a longitudinal axis of the device viewed from a first direction and a second opposite direction. In these figures, the cylindrical body (12) has been modified at its distal extremity (22) through the provision of a friction layer (68) as an alternative to the teethed engagement means described in reference to the previous embodiment, and enabling selectable or engagement between the magnetic field producing holder body (32) and the push button (23). This can be provided by any suitable material that provides sufficient friction engagement resistance to promote solidary co-rotation of a proximal outer surface (69) of the magnetic field producing holder body (32) with the cylindrical body when such a proximal outer surface (69) is engaged with the friction layer (68). Although a variety of suitable friction causing materials will enable such functionality, the applicants have found that a particularly suitable frictional engagement can be achieved when the friction layer (68) comprises a relatively high shear coefficient polymeric material, for example having a Shore hardness of between 0 Shore A, with a consistency similar to a gel, and 70 Shore D, which in contrast is a relatively rigid material. Such polymers are known as thermoplastic elastomers, or TPEs for short, and are generally classified into 6 different families:

styrene block copolymers, also known as TPS or TPE-s;
  thermoplastic polyolefin elastomers, also known as TPO or TPE-o;
  thermoplastic vulcanizates, also known as TPV or TPE-v;
  thermoplastic polyurethanes, also known as TPU;
  thermoplastic co-polyester, also known as TPC or TPE-E;
  thermoplastic polyamides, also known as TPA or TPE-a; and
  non-classified thermoplastic elastomers, also known as TPZ.

Whilst many of the above might be compatible with the envisaged functionality, the applicant has retained members from the styrene block copolymers, in particular materials made from or comprising polystyrene-b-poly(ethylene-butylene)-b-polystyrene, also known as SEBS polymers, and available for example under the brand name Kraton-G (Shell Chemicals), with a Shore A hardness of between about 40 and about 80 as the preferred material for the friction layer.

As mentioned above, the friction layer (68) is located on an inner surface (69) of the proximal extremity (22) of the cylindrical body (12). In this regard, the friction layer can be a contiguous layer, a semi-contiguous layer, or be provided in the form of an array of deposits of the friction causing material, whereby any and each of these is adapted in thickness of layer or deposit to create the required friction effect. Preferably, the friction layer (68) is an annular-shaped layer of SEBS material, which is furthermore seated on the inner surface (69) of the proximal extremity (22) of the cylindrical body via seating means (70). The seating means (70) can for example be a sealant or an adhesive, disposed and or distributed on the inner surface (69) and/or on a proximal surface of the friction layer that comes into contact with the inner surface (69). Preferably however, the applicant has found it advantageous to provide the seating means as dovetail extensions or projections (70) of the friction material, which locate, and expand into, corresponding openings provided in the proximal extremity (22) of the cylindrical body (12).

Another feature visible in the alternative embodiment illustrated by FIGS. 7 to 11, and in particular in FIGS. 10 and 11 is a spring seating guide projection (72), which extends out in a proximal direction from the proximal extremity (22) of the cylindrical body (12). This seating guide projection (72) is provided to facilitate guiding of, and appropriate seating of, the spring 62 onto the proximal extremity (22) of the cylindrical body (12).

Turning now in more detail to FIGS. 10 and 11, the magnetic field producing holder (31) has a body (32) which substantially surrounds the magnet (8). In this embodiment, the holder body (32) comprises a skirt (36), located adjacent the distal extremity (35) of the holder body (32), the skirt (36) comprising a substantially planar surface extending radially outwards from the holder body (32) and an annular peripheral wall (37) extending distally from a peripheral edge (38) of the substantially planar surface. The annular peripheral wall (37) extends down to the distal extremity, where it meets distal extremity wall (73) thereby completely encasing the magnet (8) at the distal extremity. At the proximal extremity ( ) of the magnetic field producing holder body (32), there are no teeth located on the body (32) or projections located on the bore (33). In this arrangement therefore, the skirt surface (36) of the holder body (32) forms the engagement means with a distally-facing surface of the friction layer (68) of the cylindrical body (12). The holder body (32) and the activation button body (54) are held together by frictional cooperation of bore (33) receiving holder engagement member (60). Optionally, and advantageously, said bore (33) and holder engagement member (60) are permanently connected together once assembled, for example via ultrasonic spot welding. Thus, when in the engaged position, the spring (62) pulls the holder body (32) due to the connection between bore (33) and engagement member (60) in a proximal direction towards the distal facing surface of the friction layer (68). As the spring reaches its unconstrained conformation, so the skirt surface (36) of the holder body (32) comes into contact with the distal facing surface of the friction layer (68) and is held in place to the extent that any rotational movement of the cylindrical body (12) is translated to the skirt surface (36) via the friction caused between the frictional layer and the skirt surface. In this way, the magnet (8) is frictionally bound to cylindrical body, and any rotational movement of the cylindrical body, which is connected to the dose wheel (21) of the drug delivery device, causes the magnet to rotate. If the clutch activation button is pressed, for example, by the user's thumb or another digit, the button body (54) constrains the spring (62) and moves the button body (54) and holder body (32) in an axial and distal direction, causing separation of the skirt surface (37) of the holder body (32) from the friction layer (68), and moving the clutch assembly into the disengaged position, thereby operating separation of the holder body (32) from the cylindrical body (12), allowing free and independent axial movement of the holder body in an axial direction, for example, to effect injection via abutment of the holder body (32) distal extremity (35) with the injection button, without a corresponding translation of any rotational movement to the dose setting wheel.

Whilst only two particular use scenarios have been described in detail above, the selectively engageable and disengageable clutch assembly as generally described herein enables the drug delivery device manufacturer to configure engagement and disengagement of the magnetic field producing means in a manner corresponding to the common modus operandi of their own drug delivery devices. This makes the dose control device comprising such a clutch assembly a very flexible tool for providing drug delivery device manufacturers with the possibility to not only control and verify the dose setting and actual quantity of administered drug through the use of known magnetic field detection sensors and associated data processing, but also to prevent misuse, or at least detect erroneous use of the dose control device, and equally importantly, and just as advantageously, not force a change in the user's usage habits associated with a given drug delivery device.

The invention claimed is:

1. Dose control device for a handheld pen-type injectable-drug delivery device, the handheld pen-type injectable-drug delivery device comprising an elongate body with a proximal and distal extremity, a longitudinal axis extending from the proximal extremity of the elongate body to the distal extremity of the elongate body, and a rotatable dose setting wheel located at said proximal extremity, wherein said dose control device comprises:
 a magnetic field producing means located at the proximal extremity of said elongate body;
 one or more magnetic field sensors in communication with a data processing unit located at the elongate body; and
 a clutch assembly configured to selectively move the magnetic field producing means from a first, engaged, position, to a second, disengaged, position;
 wherein said clutch assembly comprises:
 a cylindrical body having a longitudinal inner bore and a proximal extremity, wherein the magnetic field producing means is located within said bore of said cylindrical body, said cylindrical body being removably mounted in axial longitudinal alignment around said rotatable dose setting wheel with an annular wall extending within and along said bore towards the proximal extremity of the cylindrical body, wherein the cylindrical body is configured to be co-rotatable with the dose setting wheel.

2. Dose control device according to claim 1, wherein the first, engaged, position is a position in which the magnetic field producing means is held within the bore of the cylindrical body such that any rotational movement of said cylindrical body communicates directly to said magnetic field producing means causing said magnetic field producing means to rotate.

3. Dose control device according to claim 1, wherein the second, disengaged, position is a position in which the magnetic field producing means is held within the bore of the cylindrical body such that any rotational movement of said cylindrical body is not communicated to said magnetic field producing means.

4. Dose control device according to claim 1, wherein said cylindrical body has a distal extremity, said distal extremity being configured to mate with and grip an outer surface of said dose setting wheel, and the proximal extremity of the cylindrical body configured to receive at least a part of a clutch activation button.

5. Dose control device according to claim 1, wherein said annular wall is connected to an inner surface wall of said cylindrical body.

6. Dose control device according to claim 1, wherein said annular wall is connected to a cylindrical body inner surface wall via a first annular skirt which extends radially outwards from said annular wall to said cylindrical body inner surface wall.

7. Dose control device according to claim 6, wherein said annular wall, said first annular skirt and said cylindrical body inner surface wall form an annular groove for receiving at least a part of a clutch activation button.

8. Dose control device according to claim 6, wherein said annular wall further comprises a second annular skirt, located at a proximal extremity of said annular wall, which projects radially inwardly from said annular wall proximal extremity into the bore of said cylindrical body.

9. Dose control device according to claim 1, wherein said clutch assembly further comprises a magnetic field producing means holder, wherein said magnetic field producing means holder comprises a holder body having a longitudinal bore, a proximal extremity and a distal extremity, and said magnetic field producing means holder includes a body of a magnetic field producing means material.

10. Dose control device according to claim 9, wherein said magnetic field producing means holder body comprises a skirt, located adjacent the distal extremity of the holder body, said skirt comprising a substantially planar surface extending radially outwards from said holder body and an annular peripheral wall extending distally from a peripheral edge of said substantially planar surface.

11. Dose control device according to claim 10, wherein said skirt further comprises at least one seating means for the magnetic field producing means, located within an inner volume defined by the skirt, said at least one seating means being configured to receive and seat said magnetic field producing means within said skirt.

12. Dose control device according to claim 9, wherein said holder body further comprises an activation button engagement member, configured to engage and retain a clutch activation button.

13. Dose control device according to claim 12, wherein said clutch Activation button engagement member is located within the longitudinal bore of the holder body, adjacent the proximal extremity thereof.

14. Dose control device according to claim 1, wherein said clutch assembly further comprises a clutch activation button.

15. Dose control device according to claim 14, wherein said clutch activation button comprises a holder engagement member, configured to retain and engage with an activation button engagement member provided on a magnetic field producing means holder.

16. Dose control device according to claim 15, wherein said clutch assembly further comprises a pre-constrained biasing member, located between an annular skirt projecting radially inwardly from an annular wall adjacent the proximal extremity of said cylindrical body, and the clutch activation button, and said pre-constrained biasing member is seated distally on the annular skirt of the annular wall of said cylindrical body, and inserted into an inner, substantially cylindrical volume of said clutch activation button, to seat proximally against a closed proximal extremity of said inner volume.

17. Dose control device according to claim 16, wherein said pre-constrained biasing member, in the first engaged clutch assembly position, adopts a relatively unconstrained conformation, and in the second disengaged clutch assembly position, a relatively constrained conformation.

18. Dose control device according to claim 16, wherein said pre-constrained biasing member is a flat wire compression spring or a wave spring.

19. Dose control device according to claim 14, wherein the cylindrical body further comprises a frictional layer comprising a thermoplastic elastomer gel located on an inner wall of the proximal extremity of the cylindrical body, and wherein a magnetic field producing means holder body is selectively engageable with, and disengageable from, the frictional layer provided within the cylindrical body.

\* \* \* \* \*